US012642843B2

(12) United States Patent
Bystroff et al.

(10) Patent No.: US 12,642,843 B2
(45) Date of Patent: Jun. 2, 2026

---

(54) CONTRACEPTIVE VACCINE BASED ON THE SPERM-ASSOCIATED PROTEIN CATSPER

(71) Applicant: Rensselaer Polytechnic Institute, Troy, NY (US)

(72) Inventors: Christopher Bystroff, Troy, NY (US); Jean-Ju Lucia Chung, Orange, CT (US)

(73) Assignees: Rensselaer Polytechnic Institute, Troy, NY (US); Yale University, New Haven, CT (US)

( * ) Notice: Subject to any disclaimer, the term of this patent is extended or adjusted under 35 U.S.C. 154(b) by 0 days.

(21) Appl. No.: 18/437,608

(22) Filed: Feb. 9, 2024

(65) Prior Publication Data

US 2024/0424073 A1     Dec. 26, 2024

Related U.S. Application Data

(63) Continuation-in-part of application No. 17/428,865, filed as application No. PCT/US2020/017449 on Feb. 10, 2020, now abandoned.

(60) Provisional application No. 62/970,249, filed on Feb. 5, 2020, provisional application No. 62/802,922, filed on Feb. 8, 2019, provisional application No. 63/444,428, filed on Feb. 9, 2023, provisional application No. 63/551,219, filed on Feb. 8, 2024.

(51) Int. Cl.
*A61K 39/00* (2006.01)
*A61K 39/04* (2006.01)

(52) U.S. Cl.
CPC .. *A61K 39/0006* (2013.01); *A61K 2039/5258* (2013.01); *A61K 2039/6075* (2013.01)

(58) Field of Classification Search
CPC .... A61K 2039/5258; A61K 2039/5256; A61K 39/0006; A61K 2039/6075; A61P 15/16; A61P 15/18; C07K 14/705; C12N 2710/20023; C12N 7/00; C12N 2710/20022
See application file for complete search history.

(56) References Cited

U.S. PATENT DOCUMENTS

| | | |
|---|---|---|
| 2008/0014209 A1 | 1/2008 | Rice et al. |
| 2014/0223591 A1 | 8/2014 | Hay et al. |
| 2017/0107269 A1 | 4/2017 | Clapham et al. |
| 2018/0289792 A1 | 10/2018 | Ciaramella et al. |

FOREIGN PATENT DOCUMENTS

| | | |
|---|---|---|
| CN | 101747424 A | 6/2010 |
| CN | 101816799 A | 12/2011 |
| EP | 1222200 A1 | 4/2001 |
| JP | 2004535794 A | 12/2004 |
| WO | 2008025067 A1 | 3/2008 |
| WO | 03099865 A1 | 12/2023 |

OTHER PUBLICATIONS

International Search Report and The Written Opinion of the International Searching Authority, International Application No. PCT/US2020/017449, mailed Jul. 17, 2020.
Basore, D., et al., "Engineering Chimeric Virus-Like Particles for use as Vaccine Antigens," Conference abstracts, 2016 International Society for Vaccines Annual Congress, Oct. 2-4, 2016.
Jelen, M., "L1 protein [Human papillomavirus type 11]," GenBank entry, National Institute of Biotechnology Information, p. 1, Jan. 31, 2016.
Marshburn, P.B., et al., "The role of antisperm antibodies in infertility," Fertility And Sterility, vol. 61, No. 5, pp. 799-811, May 1994.
Yu, Q., et al., "Construction of a Catsper1 DNA Vaccine and Its Antifertility Effect on Male Mice," PLOS One, vol. 10, No. 5, pp. 1-14, May 18, 2015.
English Translation of Office Action in corresponding Chinese Application No. 202080013310.0 mailed Jan. 9, 2024, 12 pages.
Basore; Enhancing protein activity and stability via scaffold engineering; RPI, Aug. 10, 2018; pp. 1-129.
English Translation of Office Action (Decision of Refusal) in corresponding Japanese Application No. 2021-544400, mailed Jan. 23, 2024; 2 pages.
Honggang et al.; Inhibition of human sperm function and mouse fertilization in vitro by an antibody against cation channel of sperm 1: the contraceptive potential of its transmembrane domains and pore region; Fertility and Sterility, Sep. 2009, vol. 92, No. 3; pp. 1141-1146.
Nazari et al.; Investigation in Vitro Expression of CatSper Sub Fragment followed by Production of Polyclonal Antibody: Potential Candidate for The Next Generation of Non Hormonal Contraceptive; Cell Journal, Dec. 12, 2012, vol. 14, No. 3, pp. 215-224.
Choudhury at al.; Immunogenicity of zona pellucida glycoprotein-3 and spermatozoa YLP 1*2 peptides presented on Johnson grass mosaic virus-like particles, Vaccine, Elsevier, Amsterdam, NL, vol. 27, No. 22, May 14, 2009; pp. 2948-2953.

(Continued)

*Primary Examiner* — Bao Q Li

(74) *Attorney, Agent, or Firm* — Barclay Damon LLP; Anthony P. Gangemi

(57) ABSTRACT

A composition includes a contraceptive chimeric virus-like particle with an antigenic carrier domain and one or more antigenic regions from a sperm cell in the antigenic carrier domain, with the antigenic carrier domain including human papillomavirus L1 capsid protein and the antigenic regions including one or more structural elements of the Catsper ion channel complex. When administered to a patient, the contraceptive vaccine stimulates production of anti-sperm antibodies that, upon binding to a sperm cell, inhibit the sperm cell's motility and thus inhibit the ability of the sperm cell to fertilize an egg cell. The induced immunoinfertility of the composition can be reversed for brief or extended lengths of time by overdosing the patient with a reversal agent lacking the antigenic carrier domain but having a protein sequence substantially identical to that of the one or more antigenic regions to sequester the anti-sperm antibodies.

11 Claims, 9 Drawing Sheets

Specification includes a Sequence Listing.

(56)         References Cited

OTHER PUBLICATIONS

Honggang et al.; Immunization of male mice with B-cell epitopes in transmembrane domains of CatSper1 inhibits fertility; Fertility and Sterility, Elsevier, Amsterdam, NL, vol. 97, No. 2, 29, Nov. 29, 2011; pp. 445-452.
Office Action in corresponding European Application No. 20751996.8 mailed Jan. 3, 2025; 7 pages.
Xiaoheng Huang et al.; Research process on the localization and expression of reproductive CRISP1 in gonads and its reproductive regulatory function; Journal of Reproductive Medicine, vol. 27, Issue 10, Oct. 15, 2018, pp. 1-20.

200

202    inserting a gene for an antigenic carrier protein into a plasmid 204    preparing overlapping primers for a chimeric gene of the antigenic carrier and one or more antigenic regions from a sperm cell 206    performing a polymerase chain reaction to amplify the chimeric gene 208    synthesizing a virus-like particle from the chimeric gene

300

302 — preparing a composition including a contraceptive chimeric virus-like particle including an antigenic carrier domain and one or more antigenic regions from a sperm cell in the antigenic carrier domain 304 — administering the composition to a patient to heighten an immune response of the patient to the one or more antigenic regions

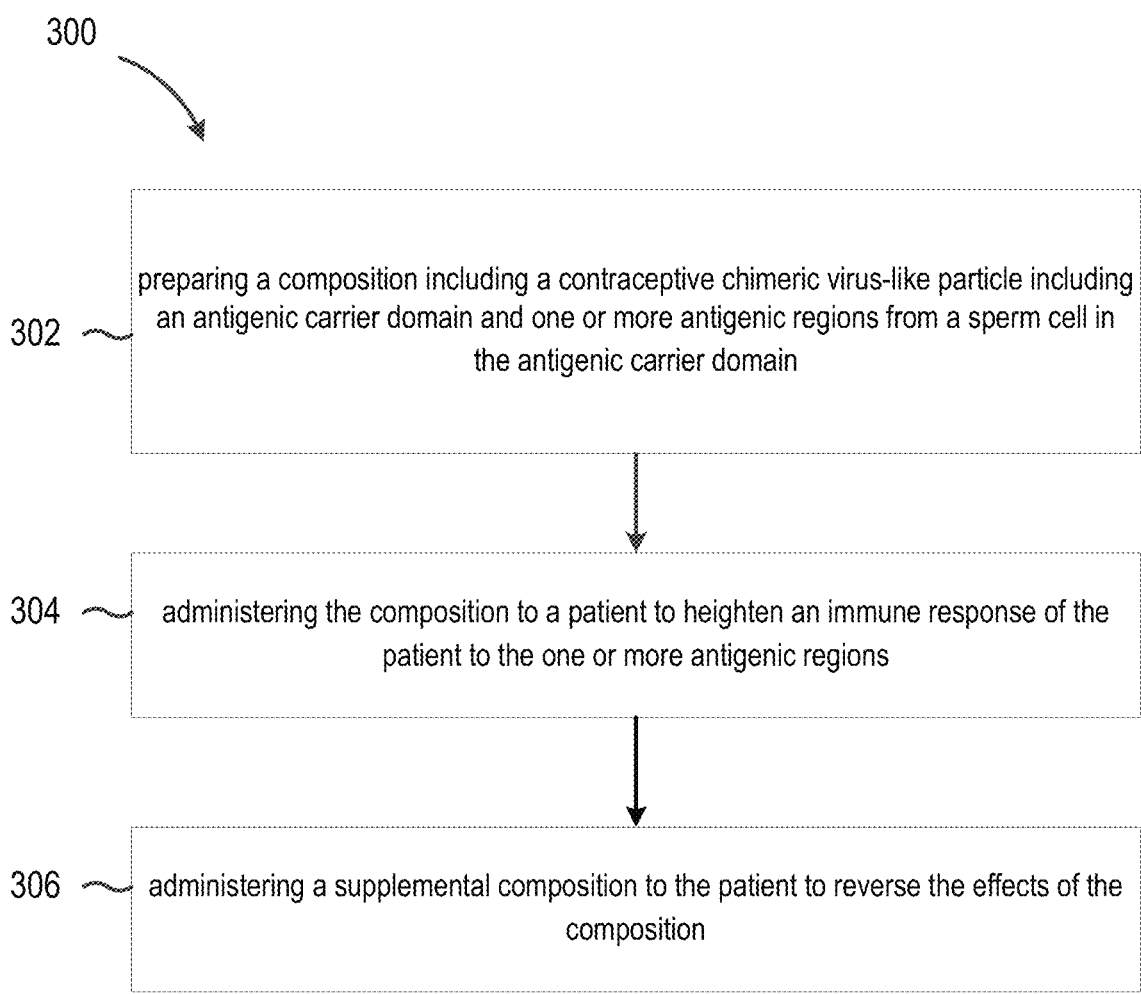

300

302 preparing a composition including a contraceptive chimeric virus-like particle including an antigenic carrier domain and one or more antigenic regions from a sperm cell in the antigenic carrier domain 304 administering the composition to a patient to heighten an immune response of the patient to the one or more antigenic regions 306 administering a supplemental composition to the patient to reverse the effects of the composition

FIG. 3B

SEQUENCE LISTING

```
Sequence total quantity: 22
SEQ ID NO: 1            moltype = AA  length = 503
FEATURE                 Location/Qualifiers
REGION                  1..503
                        note = Description of Artificial Sequence: Synthetic Peptide
source                  1..503
                        mol_type = protein
                        organism = synthetic construct
SEQUENCE: 1
STMEFMWRPS DSTVYVPPPN PVSKVVATDA YVKRTNIFYH ASSSRLLAVG HPYYSIKKVN  60
KTVVPKVSGY QYRVFKVVLP DPNKFALPDS SLFDPTTQRL VWACTGLEVG RGQPLGVGVS  120
GHPLLNKYDD VENSGGYGCG PQTFTELEIR GEWGPCGNPG QDNRVNVGMD YKQTQLCMVG  180
CAPPLGEHWG KGTQCSNTSV QNGDCPPLEL ITSVIQDGDM VDTGFGAMNF ADLQTNKSDV  240
PLDICGTVCK YPDYLQMAAD PYGDRLFFYL RKEQMFARHF FNRAGTVGEP VPDDLLVKGG  300
NNRSSVASSI YVHTPSGSLV SSEAQLFNKP YWLQKAQGHN NGICWGNHLF VTVVDTTRST  360
NMTLCASVSK SATYTNSDYK EYMRHVEEFD LQFIFQLCSI TLSAEVMAYI HTMNPSVLED  420
WNFGLSPPPN GTLEDTYRYV QSQAITCQKP TPEKEKQDPY KDMSFWEVNL KEKFSSELDQ  480
FPLGRKFLLQ SGYRGRTSAR TGI                                         503

SEQ ID NO: 2            moltype = AA  length = 505
FEATURE                 Location/Qualifiers
REGION                  1..505
                        note = Description of Artificial Sequence: Synthetic Peptide
source                  1..505
                        mol_type = protein
                        organism = synthetic construct
SEQUENCE: 2
STMEFMWRPS DSTVYVPPPN PVSKVVATDA YVKRTNIFYH ASSSRLLAVG HPYYSIKKVN  60
```

```
KTVVPKVSGY QYRVFKVVLP DPNKFALPDS SLFDPTTQRL VWACTGLEVG RGQPLGVGVS   120
GHPLLNKYDD VENSGGYGCG PREYSRSTIE GLEYNGPCGN PGQDNRVNVG MDYKQTQLCM   180
VGCAPPLGEH WGKGTQCSNT SVQNGDCPPL ELITSVIQDG DMVDTGFGAM NFADLQTNKS   240
DVPLDICGTV CKYPDYLQMA ADPYGDRLFF YLRKEQMFAR HFFNRAGTVG EPVPDDLLVK   300
GGNNRSSVAS SIYVHTPSGS LVSSEAQLFN KPYWLQKAQG HNNGICWGNH LFVTVVDTTR   360
STNMTLCASV SKSATYTNSD YKEYMRHVEE FDLQFIFQLC SITLSAEVMA YIHTMNPSVL   420
EDWNFGLSPP PNGTLEDTYR YVQSQAITCQ KPTPEKEKQD PYKDMSFWEV NLKEKFSSEL   480
DQFPLGRKFL LQSGYRGRTS ARTGI                                        505

SEQ ID NO: 3              moltype = AA   length = 499
FEATURE                   Location/Qualifiers
REGION                    1..499
                          note = Description of Artificial Sequence: Synthetic Peptide
source                    1..499
                          mol_type = protein
                          organism = synthetic construct
SEQUENCE: 3
STMEFMWRPS DSTVYVPPPN PVSKVVATDA YVKRTNIFYH ASSSRLLAVG HPYYSICGPN   60
SLSYSFYNHS LFRGPCVVPK VSGYQYRVFK VVLPDPNKFA LPDSSLFDPT TQRLVWACTG   120
LEVGRGQPLG VGVSGHPLLN KYDDVENSGG YGGNPGQDNR VNVGMDYKQT QLCMVGCAPP   180
LGEHWGKGTQ CSNTSVQNGD CPPLELITSV IQDGDMVDTG FGAMNFADLQ TNKSDVPLDI   240
CGTVCKYPDY LQMAADPYGD RLFFYLRKEQ MFARHFFNRA GTVGEPVPDD LLVKGGNNRS   300
SVASSIYVHT PSGSLVSSEA QLFNKPYWLQ KAQGHNNGIC WGNHLFVTVV DTTRSTNMTL   360
CASVSKSATY TNSDYKEYMR HVEEFDLQFI FQLCSITLSA EVMAYIHTMN PSVLEDWNFG   420
LSPPPNGTLE DTYRYVQSQA ITCQKPTPEK EKQDPYKDMS FWEVNLKEKF SSELDQFPLG   480
RKFLLQSGYR GRTSARTGI                                              499

SEQ ID NO: 4              moltype = AA   length = 499
FEATURE                   Location/Qualifiers
REGION                    1..499
                          note = Description of Artificial Sequence: Synthetic Peptide
source                    1..499
                          mol_type = protein
                          organism = synthetic construct
SEQUENCE: 4
STMEFMWRPS DSTVYVPPPN PVSKVVATDA YVKRTNIFYH ASSSRLLAVG HPYYSICGPE   60
IELMESTNTA LWPGPCVVPK VSGYQYRVFK VVLPDPNKFA LPDSSLFDPT TQRLVWACTG   120
LEVGRGQPLG VGVSGHPLLN KYDDVENSGG YGGNPGQDNR VNVGMDYKQT QLCMVGCAPP   180
LGEHWGKGTQ CSNTSVQNGD CPPLELITSV IQDGDMVDTG FGAMNFADLQ TNKSDVPLDI   240
CGTVCKYPDY LQMAADPYGD RLFFYLRKEQ MFARHFFNRA GTVGEPVPDD LLVKGGNNRS   300
SVASSIYVHT PSGSLVSSEA QLFNKPYWLQ KAQGHNNGIC WGNHLFVTVV DTTRSTNMTL   360
CASVSKSATY TNSDYKEYMR HVEEFDLQFI FQLCSITLSA EVMAYIHTMN PSVLEDWNFG   420
LSPPPNGTLE DTYRYVQSQA ITCQKPTPEK EKQDPYKDMS FWEVNLKEKF SSELDQFPLG   480
RKFLLQSGYR GRTSARTGI                                              499

SEQ ID NO: 5              moltype = AA   length = 497
FEATURE                   Location/Qualifiers
REGION                    1..497
                          note = Description of Artificial Sequence: Synthetic Peptide
source                    1..497
                          mol_type = protein
                          organism = synthetic construct
SEQUENCE: 5
STMEFMWRPS DSTVYVPPPN PVSKVVATDA YVKRTNIFYH ASSSRLLAVG HPYYSICGPG   60
TNYDIQFEFF RGPCVVPKVS GYQYRVFKVV LPDPNKFALP DSSLFDPTTQ RLVWACTGLE   120
VGRGQPLGVG VSGHPLLNKY DDVENSGGYG GNPGQDNRVN VGMDYKQTQL CMVGCAPPLG   180
EHWGKGTQCS NTSVQNGDCP PLELITSVIQ DGDMVDTGFG AMNFADLQTN KSDVPLDICG   240
TVCKYPDYLQ MAADPYGDRL FFYLRKEQMF ARHFFNRAGT VGEPVPDDLL VKGGNNRSSV   300
ASSIYVHTPS GSLVSSEAQL FNKPYWLQKA QGHNNGICWG NHLFVTVVDT TRSTNMTLCA   360
SVSKSATYTN SDYKEYMRHV EEFDLQFIFQ LCSITLSAEV MAYIHTMNPS VLEDWNFGLS   420
PPPNGTLEDT YRYVQSQAIT CQKPTPEKEK QDPYKDMSFW EVNLKEKFSS ELDQFPLGRK   480
FLLQSGYRGR TSARTGI                                                497

SEQ ID NO: 6              moltype = AA   length = 501
FEATURE                   Location/Qualifiers
REGION                    1..501
                          note = Description of Artificial Sequence: Synthetic Peptide
source                    1..501
                          mol_type = protein
                          organism = synthetic construct
SEQUENCE: 6
STMEFMWRPS DSTVYVPPPN PVSKVVATDA YVKRTNIFYH ASSSRLLAVG HPYYSIKKVN   60
KTVVPKVSGY QYRVFKVVLP DPNKFALPDS SLFDPTTQRL VWACTGLEVG RGQPLGVGVS   120
GHPLLNKYDD VENSGGYGGN PGQDNRVNVG MDYKQTQLCM VGCAPPLGEH WGKGTQCSNT   180
SVQNGDCPPL ELITSVIQDG DMVDTGFGAM NFADLQTNKS DVPLDICGTV CKYPDYLQMA   240
ADPYGDRLFF YLRKEQMFAR HFFNRAGTVG EPVPDDLLVK GGNNRSSVAS SIYVHTPSGS   300
LVSSEAQLFN KPYWLQKAQG HNNGICWGNH LFVTVVDTTR STNMTLCASV CGPRALFQDS   360
DPKRFQNGPC TYTNSDYKEY MRHVEEFDLQ FIFQLCSITL SAEVMAYIHT MNPSVLEDWN   420
FGLSPPPNGT LEDTYRYVQS QAITCQKPTP EKEKQDPYKD MSFWEVNLKE KFSSELDQFP   480
```

```
LGRKFLLQSG YRGRTSARTG I                                                    501

SEQ ID NO: 7            moltype = AA  length = 498
FEATURE                 Location/Qualifiers
REGION                  1..498
                        note = Description of Artificial Sequence: Synthetic Peptide
source                  1..498
                        mol_type = protein
                        organism = synthetic construct
SEQUENCE: 7
STMEFMWRPS DSTVYVPPPN PVSKVVATDA YVKRTNIFYH ASSSRLLAVG HPYYSIKKVN  60
KTVVPKVSGY QYRVFKVVLP DPNKFALPDS SLFDPTTQRL VWACTGLEVG RGQPLGVGVS  120
GHPLLNKYDD VENSGGYGGN PGQDNRVNVG MDYKQTQLCM VGCAPPLGEH WGKGTQCSNT  180
SVQNGDCPPL ELITSVIQDG DMVDTGFGAM NFADLQTNKS DVPLDICGTV CKYPDYLQMA  240
ADPYGDRLFF YLRKEQMFAR HFFNRAGTVG EPVPDDLLVK GGNNRSSVAS SIYVHTPSGS  300
LVSSEAQLFN KPYWLQKAQG HNNGICWGNH LFVTVVDTTR STNMTLCASV CGPQDIWKVP  360
ESSRGPCTYT NSDYKEYMRH VEEFDLQFIF QLCSITLSAE VMAYIHTMNP SVLEDWNFGL  420
SPPPNGTLED TYRYVQSQAI TCQKPTPEKE KQDPYKDMSF WEVNLKEKFS SELDQFPLGR  480
KFLLQSGYRG RTSARTGI                                                 498

SEQ ID NO: 8            moltype = AA  length = 12
FEATURE                 Location/Qualifiers
REGION                  1..12
                        note = Description of Artificial Sequence: Synthetic Peptide
source                  1..12
                        mol_type = protein
                        organism = synthetic construct
SEQUENCE: 8
QTFTELEIRG EW                                                       12

SEQ ID NO: 9            moltype = AA  length = 14
FEATURE                 Location/Qualifiers
REGION                  1..14
                        note = Description of Artificial Sequence: Synthetic Peptide
source                  1..14
                        mol_type = protein
                        organism = synthetic construct
SEQUENCE: 9
NSLSYSFYNH SLFR                                                     14

SEQ ID NO: 10           moltype = AA  length = 14
FEATURE                 Location/Qualifiers
REGION                  1..14
                        note = Description of Artificial Sequence: Synthetic Peptide
source                  1..14
                        mol_type = protein
                        organism = synthetic construct
SEQUENCE: 10
RALFQDSDPK RFQN                                                     14

SEQ ID NO: 11           moltype = AA  length = 14
FEATURE                 Location/Qualifiers
REGION                  1..14
                        note = Description of Artificial Sequence: Synthetic Peptide
source                  1..14
                        mol_type = protein
                        organism = synthetic construct
SEQUENCE: 11
EIELMESTNT ALWP                                                     14

SEQ ID NO: 12           moltype = AA  length = 14
FEATURE                 Location/Qualifiers
REGION                  1..14
                        note = Description of Artificial Sequence: Synthetic Peptide
source                  1..14
                        mol_type = protein
                        organism = synthetic construct
SEQUENCE: 12
FREYSRSTIE GLEY                                                     14

SEQ ID NO: 13           moltype = AA  length = 14
FEATURE                 Location/Qualifiers
REGION                  1..14
                        note = Description of Artificial Sequence: Synthetic Peptide
source                  1..14
                        mol_type = protein
                        organism = synthetic construct
SEQUENCE: 13
REYSRSTIEG LEYN                                                     14
```

-continued

```
SEQ ID NO: 14          moltype = AA   length = 11
FEATURE                Location/Qualifiers
REGION                 1..11
                       note = Description of Artificial Sequence: Synthetic Peptide
source                 1..11
                       mol_type = protein
                       organism = synthetic construct
SEQUENCE: 14
QDIWKVPESS R                                                    11

SEQ ID NO: 15          moltype = AA   length = 12
FEATURE                Location/Qualifiers
REGION                 1..12
                       note = Description of Artificial Sequence: Synthetic Peptide
source                 1..12
                       mol_type = protein
                       organism = synthetic construct
SEQUENCE: 15
GTNYDIQFEF FR                                                   12

SEQ ID NO: 16          moltype = AA   length = 16
FEATURE                Location/Qualifiers
REGION                 1..16
                       note = Description of Artificial Sequence: Synthetic Peptide
source                 1..16
                       mol_type = protein
                       organism = synthetic construct
SEQUENCE: 16
RKIKGNHSAY LHFADG                                               16

SEQ ID NO: 17          moltype = AA   length = 13
FEATURE                Location/Qualifiers
REGION                 1..13
                       note = Description of Artificial Sequence: Synthetic Peptide
source                 1..13
                       mol_type = protein
                       organism = synthetic construct
SEQUENCE: 17
GVTDRGDLEN WGN                                                  13

SEQ ID NO: 18          moltype = AA   length = 13
FEATURE                Location/Qualifiers
REGION                 1..13
                       note = Description of Artificial Sequence: Synthetic Peptide
source                 1..13
                       mol_type = protein
                       organism = synthetic construct
SEQUENCE: 18
QEELDKRKFT VSR                                                  13

SEQ ID NO: 19          moltype = AA   length = 12
FEATURE                Location/Qualifiers
REGION                 1..12
                       note = Description of Artificial Sequence: Synthetic Peptide
source                 1..12
                       mol_type = protein
                       organism = synthetic construct
SEQUENCE: 19
RTNSYLGQKH YE                                                   12

SEQ ID NO: 20          moltype = AA   length = 14
FEATURE                Location/Qualifiers
REGION                 1..14
                       note = Description of Artificial Sequence: Synthetic Peptide
source                 1..14
                       mol_type = protein
                       organism = synthetic construct
SEQUENCE: 20
YTDFQMDERE YAME                                                 14

SEQ ID NO: 21          moltype = AA   length = 20
FEATURE                Location/Qualifiers
REGION                 1..20
                       note = Description of Artificial Sequence: Synthetic Peptide
source                 1..20
                       mol_type = protein
                       organism = synthetic construct
SEQUENCE: 21
```

-continued

---

| RRVKDQNRGK VRVAQKHPET | 20 |

SEQ ID NO: 22      moltype = AA  length = 18
FEATURE              Location/Qualifiers
REGION               1..18
                    note = Description of Artificial Sequence: Synthetic Peptide
source               1..18
                    mol_type = protein
                    organism = synthetic construct
SEQUENCE: 22
DGTVYLRTED EFTKLDES                18

CONTRACEPTIVE VACCINE BASED ON THE SPERM-ASSOCIATED PROTEIN CATSPER

CROSS REFERENCE TO RELATED APPLICATION(S)

This application is a continuation-in-part of U.S. Utility patent application Ser. No. 17/428,865, filed Aug. 5, 2021, which is a national stage filing of International Patent Application No. PCT/US2020/017449, filed Feb. 10, 2020, which claims the benefit of U.S. Provisional Application Nos. 62/802,922, filed Feb. 8, 2019, and 62/970,249, filed Feb. 5, 2020, which are incorporated by reference as if disclosed herein in their entireties. This application also claims the benefit of U.S. Provisional Patent Application Nos. 63/444,428, filed Feb. 9, 2023, and 63/551,219, filed Feb. 8, 2024, which are incorporated by reference as if disclosed herein in their entireties.

BACKGROUND

Almost half of all pregnancies worldwide are unwanted or mistimed. Current long-acting reversible contraceptive technology is focused on hormonal methods or surgery. Despite their overall effectiveness, there are myriad drawbacks to the contraceptive technologies available to women and men. By way of example, some women cannot tolerate hormonal contraception. Further, hormonal methods often require significant discipline or discomfort in the patient. For example, a regimen of pills or patches need to be taken or applied at regular intervals over the time that the contraceptive effect is desired. Implanted or intrauterine devices can cause mild to severe side-effects and complications, and still may require a clinical visit for reversal or for reimplantation.

What is desired, therefore, is an effective, long-lasting, and reversible contraceptive treatment with increased ease of use that also reduces the treatment-related burden on the patients desiring the contraceptive effects.

SUMMARY

Accordingly, some embodiments of the present disclosure relate to a contraceptive chimeric virus-like particle including an antigenic carrier domain and one or more antigenic regions from a sperm cell in the antigenic carrier domain. In some embodiments, the antigenic carrier domain includes one or more capsid proteins. In some embodiments, the one or more capsid proteins include L1 from human papillomavirus. In some embodiments, CGP amino acid residues are adjacent the N-terminal end of the one or more antigenic regions and GPC amino acid residues are adjacent the C-terminal end of the one or more antigenic regions. In some embodiments, the one or more antigenic regions include structural elements of the Catsper ion channel complex. In some embodiments, the structural elements include at least a portion of one or more loops positioned between the transmembrane helical segments of the Catsper ion channel complex. In some embodiments, the structural elements include at least a portion of: the loop between Catsper1 s1 and Catsper1 s2, the loop between Catsper2 s5 and Catsper2 p-loop, the loop between Catsper1 s3 and Catsper1 s4, the loop between Catsper2 s1 and Catsper2 s2, the loop between Catsper3 s1 and Catsper3 s2, the loop between Catsper1 s5 and Catsper1 p-loop, the loop between Catsper2 p-loop and Catsper2 s6, the loop between Catsper3 s3 and Catsper3 s4, the loop between Catsper3 s5 and Catsper3 p-loop, the loop between Catsper3 p-loop and Catsper3 s6, the loop between Catsper4 s1 and Catsper4 s2, the loop between Catsper4 p-loop and Catsper4 s6, Catsperδ loop 785-805, Catsperε loop 331-348, or combinations thereof. In some embodiments, the virus-like particle includes SEQ. ID. NO.: 1, SEQ. ID. NO.: 2, SEQ. ID. NO.: 3, SEQ. ID. NO.: 4, SEQ. ID. NO.: 5, SEQ. ID. NO.: 6, SEQ. ID. NO.: 7, or combinations thereof.

Some embodiments of the present disclosure relate to a method of making a contraceptive chimeric virus-like particle including inserting a gene for an antigenic carrier protein into a plasmid, preparing overlapping primers for a chimeric gene of the antigenic carrier and one or more antigenic regions from a sperm cell, performing a polymerase chain reaction to amplify the chimeric gene, and synthesizing a virus-like particle from the chimeric gene. In some embodiments, the one or more antigenic regions include structural elements of the Catsper ion channel complex. In some embodiments, the structural elements include at least a portion of one or more loops positioned between the transmembrane helical segments of the Catsper ion channel complex. In some embodiments, the structural elements include at least a portion of: the loop between Catsper1 s1 and Catsper1 s2, the loop between Catsper2 s5 and Catsper2 p-loop, the loop between Catsper1 s3 and Catsper1 s4, the loop between Catsper2 s1 and Catsper2 s2, the loop between Catsper3 s1 and Catsper3 s2, the loop between Catsper1 s5 and Catsper1 p-loop, the loop between Catsper2 p-loop and Catsper2 s6, the loop between Catsper3 s3 and Catsper3 s4, the loop between Catsper3 s5 and Catsper3 p-loop, the loop between Catsper3 p-loop and Catsper3 s6, the loop between Catsper4 s1 and Catsper4 s2, the loop between Catsper4 p-loop and Catsper4 s6, Catsperδ loop 785-805, Catsperε loop 331-348, or combinations thereof. In some embodiments, the virus-like particle includes SEQ. ID. NO.: 1, SEQ. ID. NO.: 2, SEQ. ID. NO.: 3, SEQ. ID. NO.: 4, SEQ. ID. NO.: 5, SEQ. ID. NO.: 6, SEQ. ID. NO.: 7, or combinations thereof.

Some embodiments of the present disclosure relate to a method for providing contraceptive treatment to a patient including preparing a composition including a contraceptive chimeric virus-like particle including an antigenic carrier domain and one or more antigenic regions from a sperm cell in the antigenic carrier domain, and administering the composition to a patient to heighten an immune response of the patient to the one or more antigenic regions. In some embodiments, the antigenic carrier domain includes L1 from human papillomavirus. In some embodiments, the one or more antigenic regions include structural elements of the Catsper ion channel complex, wherein the structural elements include at least a portion of: the loop between Catsper1 s1 and Catsper1 s2, the loop between Catsper2 s5 and Catsper2 p-loop, the loop between Catsper1 s3 and Catsper1 s4, the loop between Catsper2 s1 and Catsper2 s2, the loop between Catsper3 s1 and Catsper3 s2, the loop between Catsper1 s5 and Catsper1 p-loop, the loop between Catsper2 p-loop and Catsper2 s6, the loop between Catsper3 s3 and Catsper3 s4, the loop between Catsper3 s5 and Catsper3 p-loop, the loop between Catsper3 p-loop and Catsper3 s6, the loop between Catsper4 s1 and Catsper4 s2, the loop between Catsper4 p-loop and Catsper4 s6, Catsperδ loop 785-805, Catsperε loop 331-348, or combinations thereof. In some embodiments, the one or more antigenic regions includes SEQ. ID. NO.: 8, SEQ. ID. NO.: 9, SEQ. ID. NO.: 10, SEQ. ID. NO.: 11, SEQ. ID. NO.: 12, SEQ. ID. NO.: 13, SEQ. ID. NO.: 14, SEQ. ID. NO.: 15, SEQ. ID. NO.: 16, SEQ. ID. NO.: 17, SEQ. ID. NO.: 18, SEQ. ID.

NO.: 19, SEQ. ID. NO.: 20, SEQ. ID. NO.: 21, SEQ. ID. NO.: 22, or combinations thereof. In some embodiments, the composition is administered subcutaneously, intravenously, intranasally, or combinations thereof. In some embodiments, the method further includes administering a supplemental composition to the patient to reverse the effects of the composition, the supplemental composition including a reversal agent having a protein sequence substantially identical to that of the one or more antigenic regions. In some embodiments, the reversal agent includes one or more peptides, the one or more peptides include SEQ. ID. NO.: 8, SEQ. ID. NO.: 9, SEQ. ID. NO.: 10, SEQ. ID. NO.: 11, SEQ. ID. NO.: 12, SEQ. ID. NO.: 13, SEQ. ID. NO.: 14, SEQ. ID. NO.: 15, SEQ. ID. NO.: 16, SEQ. ID. NO.: 17, SEQ. ID. NO.: 18, SEQ. ID. NO.: 19, SEQ. ID. NO.: 20, SEQ. ID. NO.: 21, SEQ. ID. NO.: 22, or combinations thereof.

BRIEF DESCRIPTION OF THE DRAWINGS

The drawings show embodiments of the disclosed subject matter for the purpose of illustrating the invention. However, it should be understood that the present application is not limited to the precise arrangements and instrumentalities shown in the drawings, wherein:

FIG. 3B is a chart of a method of providing contraceptive treatment to a patient according to some embodiments of the present disclosure;

DETAILED DESCRIPTION

Figure 1:
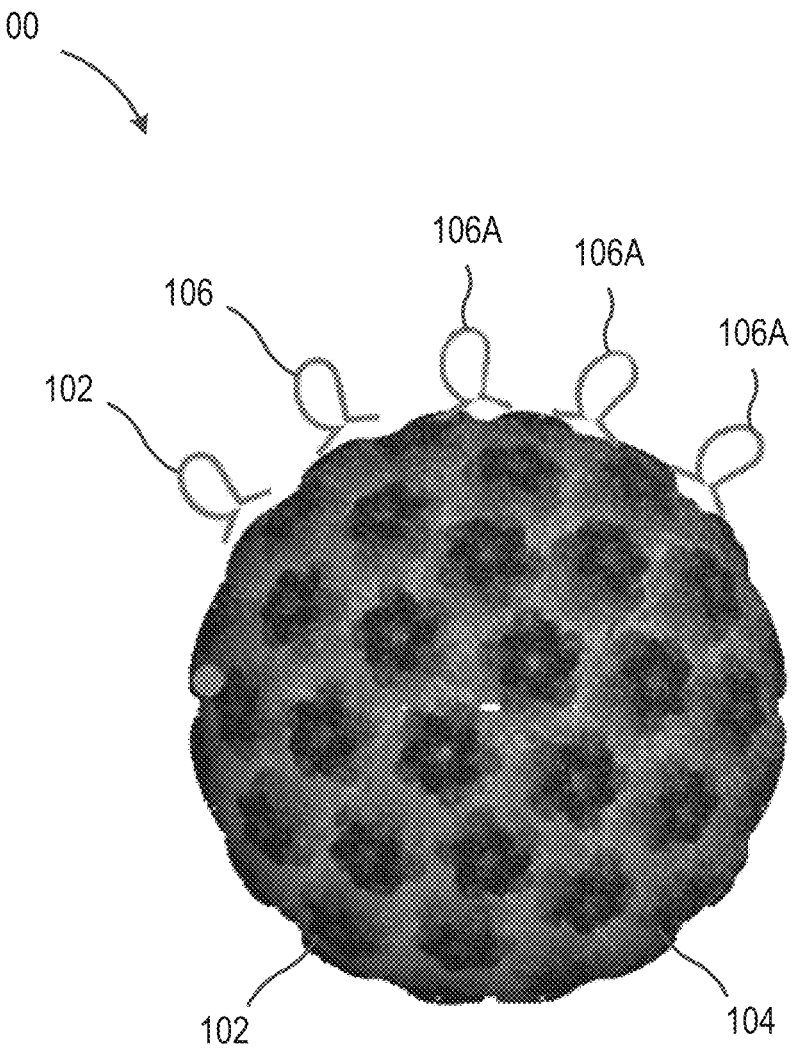
FIG. 1 is a schematic representation of a contraceptive chimeric virus-like particle according to some embodiments of the present disclosure.

Referring now to FIG. 1, some embodiments of the present disclosure are directed to a vaccine for providing contraceptive treatment to an individual, user, patient, etc. In some embodiments, the contraceptive vaccine provides contraceptive benefits to the user with an effectiveness substantially equivalent to traditional hormonal contraceptives, implanted contraceptives, physical contraceptives, etc. In some embodiments, the contraceptive vaccine heightens an immune response of the user to a structure present on sperm cells. In some embodiments, the contraceptive vaccine heightens an immune response of the user to a structure of a protein or combination of proteins present on sperm cells. In some embodiments, the contraceptive vaccine stimulates production of anti-sperm antibodies in the user. In some embodiments, the contraceptive vaccine stimulates production of anti-sperm antibodies that, upon binding to a sperm cell, inhibit the ability of the sperm cell to fertilize an egg cell. In some embodiments, the contraceptive vaccine stimulates production of anti-sperm antibodies that, upon binding to a sperm cell, inhibit the sperm cell's motility. Without wishing to be bound by theory, when administered to women, the contraceptive vaccine stimulates production of anti-sperm antibodies, e.g., in the vaginal mucosa, which bind sperm and prevent hyperactive motility in the sperm, rendering the sperm incapable of penetrating an egg. Again without wishing to be bound by theory, when administered to men, the contraceptive vaccine stimulates production of anti-sperm antibodies, e.g., in the epidydimis, which render the sperm substantially inert.

In some embodiments, the contraceptive vaccine includes a contraceptive chimeric virus-like particle (VLP) 100. In some embodiments, VLP 100 includes two or more domains 102. In some embodiments, VLP 100 includes an antigenic carrier domain 104. In some embodiments, antigenic carrier domain 104 includes one or more capsid proteins. In some embodiments, the one or more capsid proteins include L1 from human papillomavirus.

In some embodiments, VLP 100 includes an antigenic domain 106. In some embodiments, antigenic domain 106 includes one or more antigenic regions 106A. In some embodiments, antigenic regions 106A are positioned within the antigenic carrier domain 104. In some embodiments, antigenic regions 106A satisfy one or more of the following: are exposed on or about the sperm cell outer surface, are present only in sperm cells and in no other tissue in the human body, and are required for sperm function. In some embodiments, antigenic regions 106A include structural features or portions of structural features from a sperm cell. In some embodiments, antigenic regions 106A include structural elements of a protein or combination of proteins present on sperm cells. In some embodiments, antigenic regions 106A are present on sperm cell flagellum. In some embodiments, antigenic regions 106A include structural elements of the Catsper ion channel complex. In some embodiments, antigenic regions 106A include at least a portion of one or more loops positioned between the transmembrane helical segments of the Catsper ion channel complex. In some embodiments, antigenic regions 106A include at least a portion of: the loop between Catsper1 s1 and Catsper1 s2, the loop between Catsper2 s5 and Catsper2 p-loop, the loop between Catsper1 s3 and Catsper1 s4, the loop between Catsper2 s1 and Catsper2 s2, the loop between Catsper3 s1 and Catsper3 s2, the loop between Catsper1 s5 and Catsper1 p-loop, the loop between Catsper2 p-loop and Catsper2 s6, the loop between Catsper3 s3 and Catsper3 s4, the loop between Catsper3 s5 and Catsper3 p-loop, the loop between Catsper3 p-loop and Catsper3 s6, the loop between Catsper4 s1 and Catsper4 s2, the loop between Catsper4 p-loop and Catsper4 s6, Catsperδ loop 785-805, Catsperε loop 331-348, or combinations thereof. In some embodiments, antigenic regions 106A include SEQ. ID. NO.: 8, SEQ. ID. NO.: 9, SEQ. ID. NO.: 10, SEQ. ID. NO.: 11, SEQ. ID. NO.: 12, SEQ. ID. NO.: 13, SEQ. ID. NO.: 14, SEQ. ID. NO.: 15, SEQ. ID. NO.: 16, SEQ. ID. NO.: 17, SEQ. ID. NO.: 18, SEQ. ID. NO.: 19, SEQ. ID. NO.: 20, SEQ. ID. NO.: 21, SEQ. ID. NO.: 22, or combinations thereof.

In some embodiments, CGP amino acid residues are adjacent the N-terminal end of antigenic regions 106A. In some embodiments, GPC amino acid residues are adjacent the C-terminal end of one or more antigenic regions 106A. Without wishing to be bound by theory, these additional residues help stabilize antigenic regions 106A within antigenic carrier domain 104. In some embodiments, VLP 100 include SEQ. ID. NO.: 1, SEQ. ID. NO.: 2, SEQ. ID. NO.: 3, SEQ. ID. NO.: 4, SEQ. ID. NO.: 5, SEQ. ID. NO.: 6, SEQ. ID. NO.: 7, or combinations thereof.

5

In some embodiments, VLP 100 is included in a composition. In some embodiments, the composition includes one or more preservatives, stabilizers, wetting agents, emulsifiers, buffers, fillers, etc. In some embodiments, the composition is configured for administration to a user subcutaneously, intravenously, intranasally, or combinations thereof.

Figure 2:
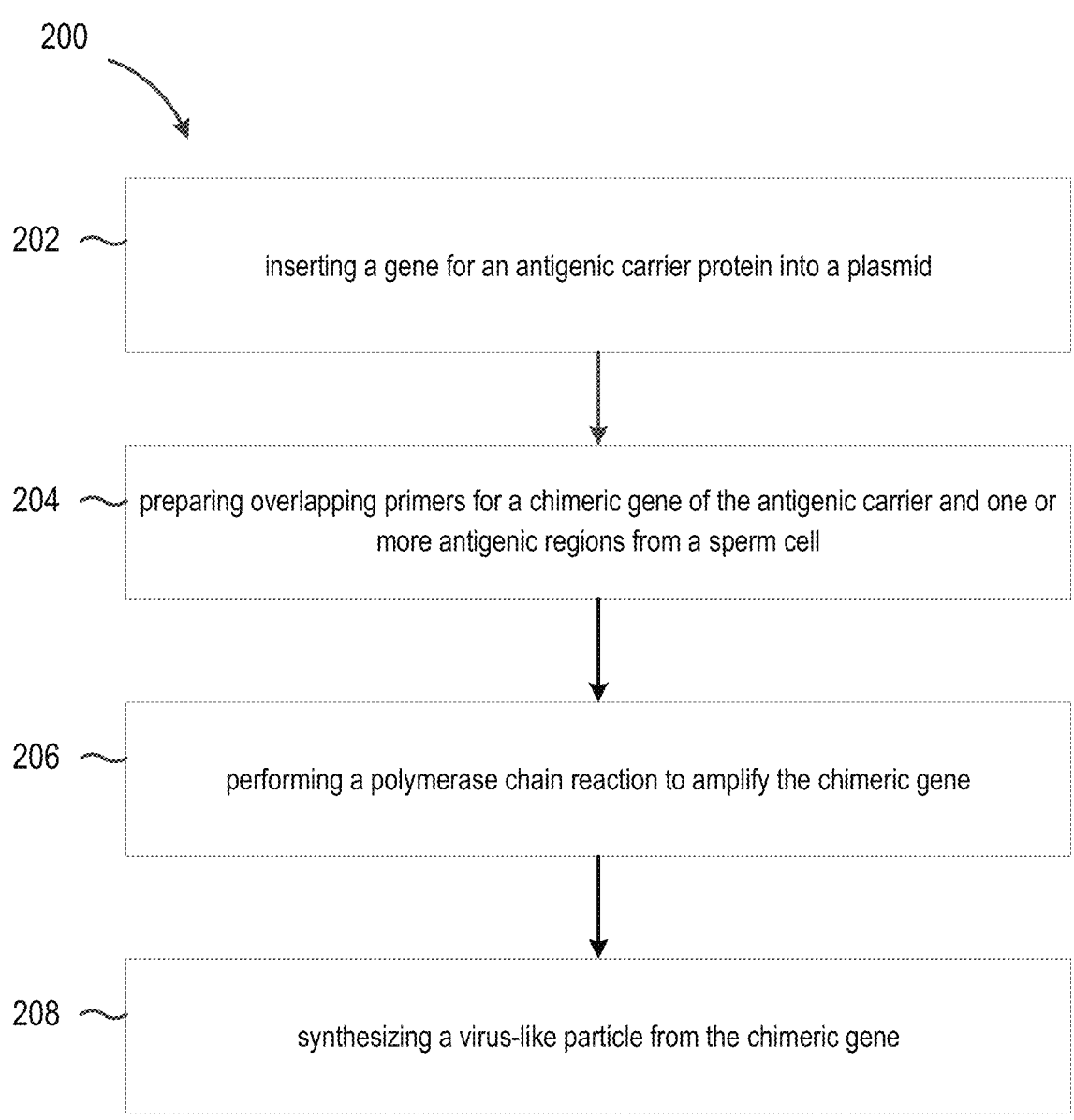
FIG. 2 is a chart of a method of making a contraceptive chimeric virus-like particle according to some embodiments of the present disclosure.

Referring now to FIG. 2, some embodiments of the present disclosure are directed to a method 200 of making a contraceptive chimeric VLP. At 202, a gene for an antigenic carrier protein is inserted into a plasmid. At 204, overlapping primers for a chimeric gene of the antigenic carrier and one or more antigenic regions from a sperm cell are prepared. As discussed above, in some embodiments, the one or more antigenic regions include structural elements of the Catsper ion channel complex, e.g., the structural elements include at least a portion of one or more loops positioned between the transmembrane helical segments of the complex. In some embodiments, the structural elements include at least a portion of: the loop between Catsper1 s1 and Catsper1 s2, the loop between Catsper2 s5 and Catsper2 p-loop, the loop between Catsper1 s3 and Catsper1 s4, the loop between Catsper2 s1 and Catsper2 s2, the loop between Catsper3 s1 and Catsper3 s2, the loop between Catsper1 s5 and Catsper1 p-loop, the loop between Catsper2 p-loop and Catsper2 s6, the loop between Catsper3 s3 and Catsper3 s4, the loop between Catsper3 s5 and Catsper3 p-loop, the loop between Catsper3 p-loop and Catsper3 s6, the loop between Catsper4 s1 and Catsper4 s2, the loop between Catsper4 p-loop and Catsper4 s6, Catsperδ loop 785-805, Catsperε loop 331-348, or combinations thereof. At 206, a polymerase chain reaction is performed to amplify the chimeric gene. At 208, a VLP is synthesized from the chimeric gene. In some embodiments, the VLP is synthesized in bacterial or yeast cell culture. In some embodiments, the VLP includes SEQ. ID. NO.: 1, SEQ. ID. NO.: 2, SEQ. ID. NO.: 3, SEQ. ID. NO.: 4, SEQ. ID. NO.: 5, SEQ. ID. NO.: 6, SEQ. ID. NO.: 7, or combinations thereof. In some embodiments, the VLP folds spontaneously. In some embodiments, the VLP is one or more of VLP 100 discussed above.

Figure 3A:
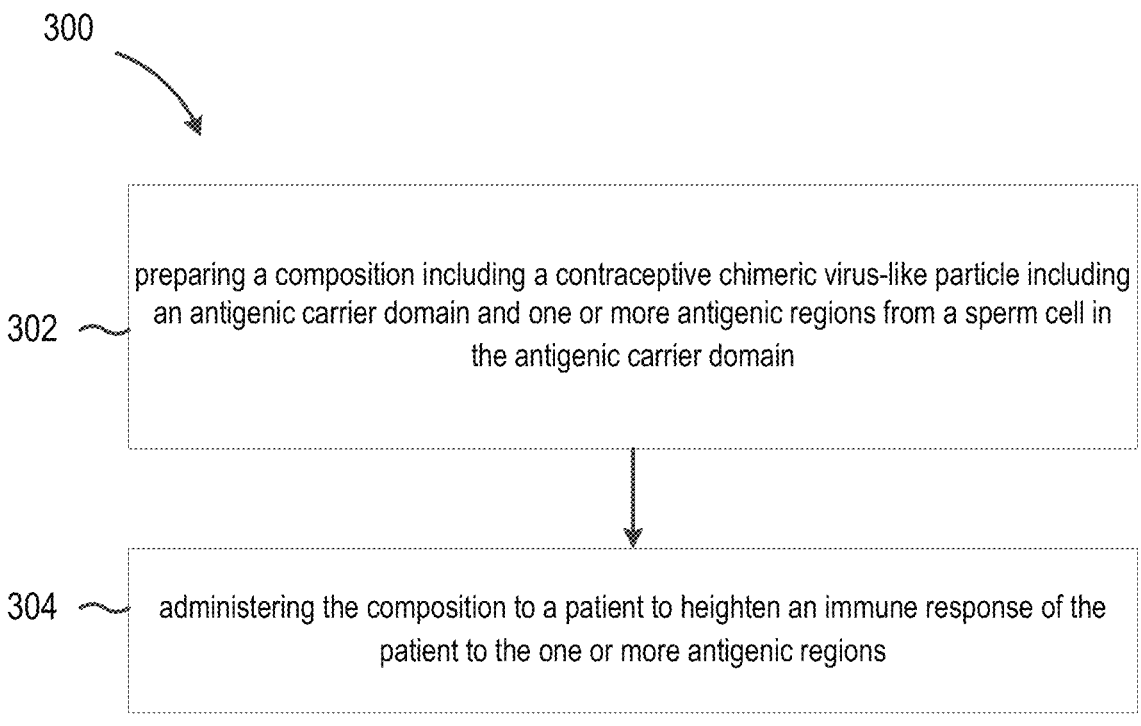
FIG. 3A is a chart of a method of providing contraceptive treatment to a patient according to some embodiments of the present disclosure.

Referring now to FIG. 3A, some embodiments of the present disclosure are directed to a method 300 for providing contraceptive treatment to a patient. At 302, a composition including a contraceptive chimeric VLP including an antigenic carrier domain and one or more antigenic regions from a sperm cell in the antigenic carrier domain is prepared. In some embodiments, the chimeric VLP is one or more of VLP 100 discussed above. At 304, the composition is administered to a patient to heighten an immune response of the patient to the one or more antigenic regions. In some embodiments, the composition is administered to the patient subcutaneously, intravenously, intranasally, or combinations thereof. Without wishing to be bound by theory, contraceptive immunity is expected to last for about 1 to about 9 years, based on prior experience for women immunized against HPV.

Referring now to FIG. 3B, in some embodiments, at 306, a supplemental composition is administered to the patient to reverse the effects of the composition. In some embodiments, the supplemental composition includes a reversal agent having a protein sequence substantially identical to that of the one or more antigenic regions. In some embodiments, the supplemental composition does not include an antigenic carrier protein. In some embodiments, the reversal agent includes one or more peptides, the one or more peptides including SEQ. ID. NO.: 8, SEQ. ID. NO.: 9, SEQ. ID. NO.: 10, SEQ. ID. NO.: 11, SEQ. ID. NO.: 12, SEQ. ID. NO.: 13, SEQ. ID. NO.: 14, SEQ. ID. NO.: 15, SEQ. ID. NO.: 16, SEQ. ID. NO.: 17, SEQ. ID. NO.: 18, SEQ. ID. NO.: 19, SEQ. ID. NO.: 20, SEQ. ID. NO.: 21, SEQ. ID. NO.: 22, or combinations thereof. In some embodiments, the supplemental composition includes one or more preservatives, stabilizers, wetting agents, emulsifiers, buffers, fillers, etc. Without wishing to be bound by theory, the induced immunoinfertility of the composition is reversed by sequestering the anti-sperm antibodies using overdosing with the supplemental composition. In some embodiments, in the event that a sperm-immune individual wishes to recover fertility for a short period of time, a window of fertility may be created by the application of a reversal agent.

EXAMPLE

Design of chimeric L1. By way of example, chimeric L1 VLP forming proteins that include short antigenic segments from the sperm cationic ion channel Catsper were prepared. Antigenic segments of Catsper were predicted by identifying extracellular loops using the homology model. Site of insertion into the L1 gene were identified by multiple sequence alignment of homolog papilloma virus L1 sequences. Three candidate insertion sites were identified as sites of natural insertion/deletion. Bracketing CGP..GPC sequences were added to stabilize the inserted loop. DNA sequences were designed using DNA Works.

Cloning of chimeric L1. The gene for HPV Type 11 L1 was synthesized using the assembly PCR method. The gene was inserted into the pET28a+ vector at NdeI and EcoRI cloning sites. The plasmid was grown and purified from cell culture using *Escherichia coli* strain DH5α. Chimeric constructs were made by amplifying the plasmid (inverse PCR) using overlapping oligos including the sequence of the desired antigenic region. Amplicons were transformed into DH5α cells for plasmid amplification, and were moved into BL21 (DE3) pLysS cells for protein expression.

Isolation of inclusion body (IB). Recombinant proteins L1 protein of HPV Type 11 (L1), L1 with Catsper loop S3-S4 (P1), and L1 with Catsper-Epsilon loop 331-348 (C5) were expressed in *E. coli*. Recombinant proteins (L1, P1 and C5) were purified from inclusion bodies (IBs) isolated from *E. coli* B121 (DE3) transformed by the plasmid constructs pET28a-L1-P1 and pET28a-L1-C5. Cells from a 500 ml culture of transformed *E. coli* cells, after induction for recombinant protein synthesis, were harvested. The wet cell biomass, approximately 1 g in weight, was suspended in 25 ml of buffer (50 mM Tris, 50 mM NaCl, pH 9.5) by gentle stirring. The suspension was subjected to sonication (15 cycles, 10 Sec on and 10 sec off in ice) and then centrifuged for 20 min at 12,000 g at 4° C. to pellet the IBs. Harvested IBs were washed twice with wash buffer 50 mM Tris (pH 9.5).

Solubilization and refolding. Comparatively purified IBs were solubilized in 5 ml of solubilization buffer (50 mM Tris (pH 9.5), 50 mM NaCl, 50 mM NaCl, 8 M urea), and stirred gently at room temperature for 2 h. The resultant suspension was centrifuged at 11000 rpm for 36 min at 25° C. to collect total soluble protein. Solubilized IBs were refolded in 10 volumes of ice cold refolding buffer (50 mM Tris, 50 mM NaCl, 5% B-mercaptoethanol and 100 mM L-Arginine (pH 9.5)) using pulsatile dilution method at a rate of approximately 0.1 ml/min. Refolded protein was centrifuged at 11000 rpm for 45 minutes at 4° C.

Dialysis and in vitro assembly of Virus-like particles (VLP). Refolded protein was filtered through 0.2 μm filter (VWR) and dialyzed against dialysis buffer (50 mM Tris, 100 mM NaCl, pH 9.5) using 12-14 kDa cut off dialysis membrane (Spectra/Por, VWR) at 4° C. NaCl concentration was increased stepwise up to 500 mM after three changes of dialysis buffer at 3 h intervals. Final dialysis was carried out for 2 h against high salt buffer (50 mM Tris, 500 mM NaCl, pH 9.5).

Characterization of exemplary embodiments of the present disclosure was done on the basis of Sodium dodecyl sulfate polyacrylamide gel electrophoresis (SDS-PAGE), western blot, and transmission electron microscopy (TEM). SDS-PAGE was performed according to standard procedure of Laemmli to analyze expression and purity of the recombinant proteins. Protein bands were developed by Coomassie Brilliant blue staining. Total cell lysate containing the recombinant protein was resolved on 12% SDS-PAGE. For Western blot analysis, proteins were resolved on 12% SDS-PAGE, and electro-transferred onto a polyvinylidine fluoride (PVDF) membrane. Immunoreactive bands were visualized by developing with diaminobenzidine tetrahydrochloride (DAB) (Roche Diagnostics GmbH, 11718096001) in the presence of hydrogen peroxide.

Figure 4:
FIG. 4 are transmission electron microscopy images of chimeric constructs consistent with embodiments of the present disclosure.

Referring now to FIG. 4, TEM images for chimeric constructs according to some embodiments of the present disclosure are shown are shown. A negative staining method was deployed using uranyl acetate (Electron microscopy Sciences, Catalogue No. 22400-4). A carbon coated 300 mesh copper grid (Ted Pella Inc, 01813-F) was used on which samples were adhered using air dry method, followed by staining and re-drying. Samples were examined on a JOEL 1200 EX transmission electron microscope running at 200 kV at 300,000× magnification. The TEM images show VLPs of the correct size for both L1-P1 and L1-C5 chimeric constructs. Segmentation of 5 nm capsomere subunits is evidence that the VLPs are well ordered.

Figure 5A:
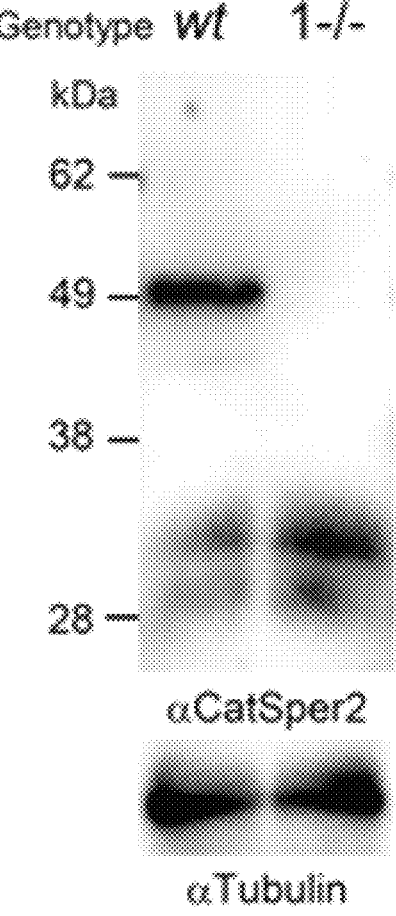
FIGS. 5A-5C portray testing results demonstrating the specificity and inhibitory effect of CatSper antibodies.
Figure 5B:
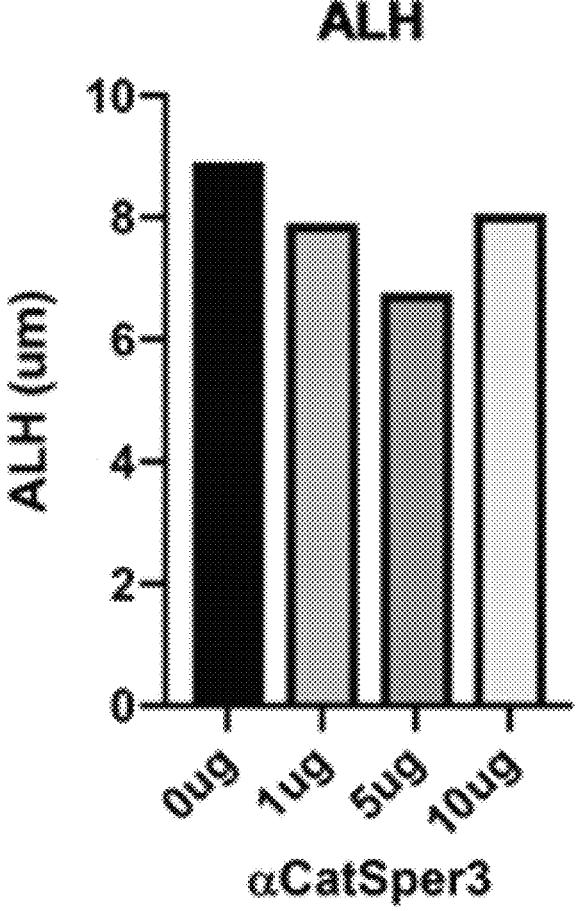
Figure 5C:
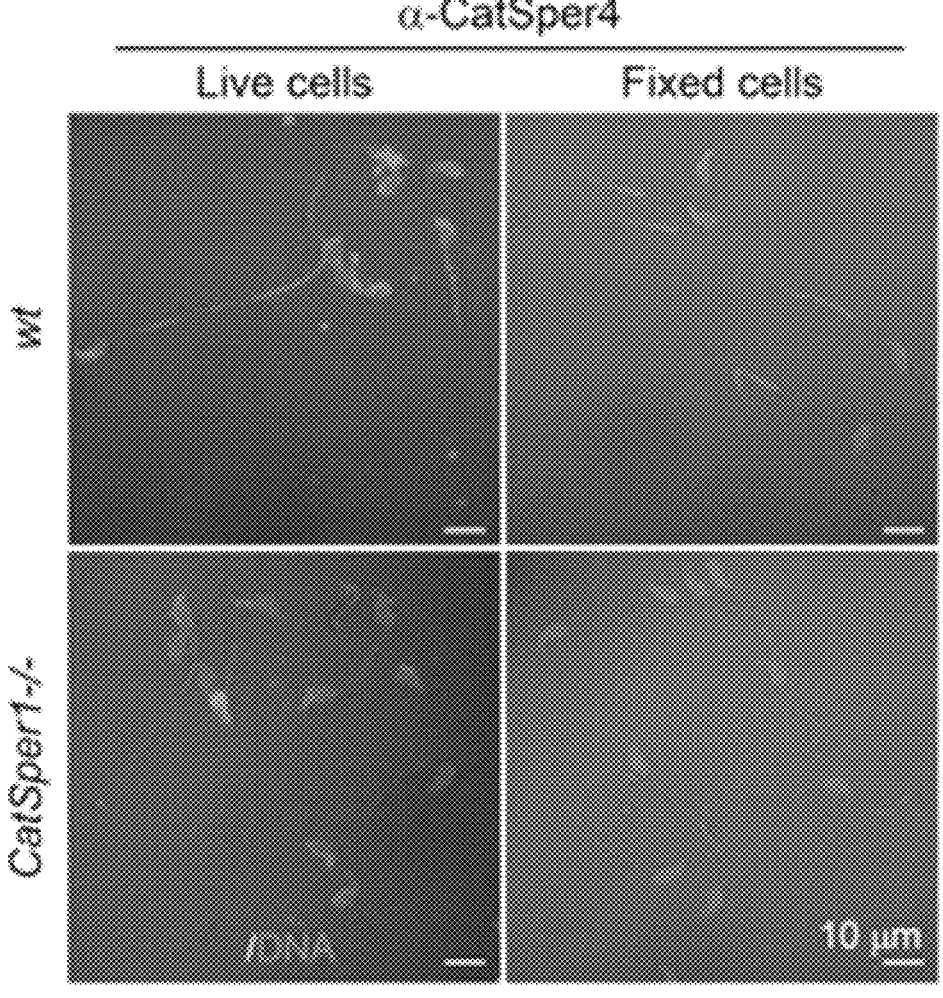

Referring now to FIGS. 5A-C, CatSper peptide antibodies configured to specifically target CatSper in fixed sperm cells were analyzed for sperm motility inhibition and thus contraceptive effect. The specificity of CatSper antibodies detecting each CatSper subunit using CatSper1-knockout mouse sperm (lacking CatSper components) as the negative control was also tested. The dose response effect of the CatSper antibodies on the sperm motility was performed. CatSper2 was specifically recognized by CatSper2 antibodies via the extracellular loop mCs2-s5P (see FIG. 5A). The amplitude of lateral head displacement (ALH) was measured by a computerized automatic sperm analyzer tracking system, which showed dose-dependent inhibition by antibodies against the CatSper3 peptide mCs3-s5P (see FIG. 5B). It was found that many of the antibodies tested worked best at 5 µg/ml to modestly yet significantly decrease hyperactivated motility when used alone. Antibody successfully detected the corresponding CatSper subunit (CatSper4) in both live and fixed cells (see FIG. 5C).

Figure 6:
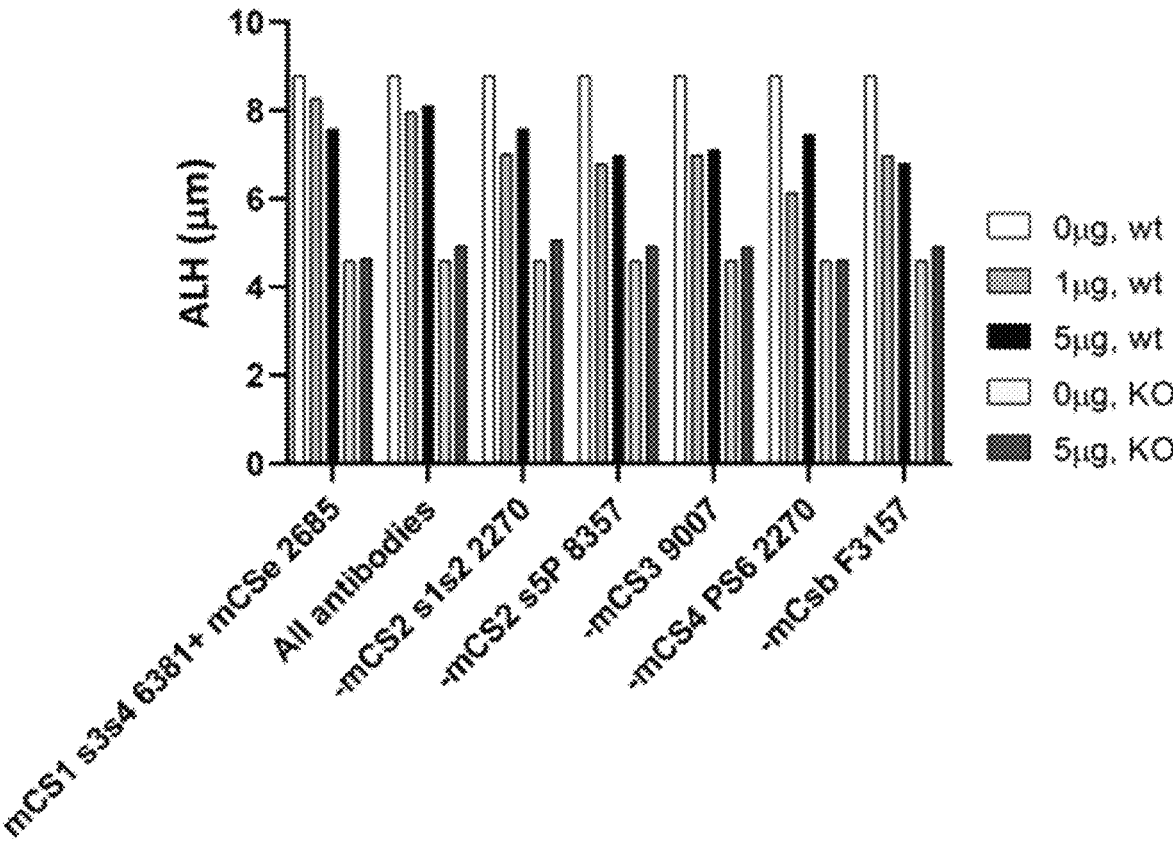
FIG. 6 is a graph portraying testing results demonstrating the effect of CatSper antibodies on sperm motility, measured as the amplitude of lateral head displacement (ALH).

Referring now to FIG. 6, multiple CatSper antibodies in different combinations were tested. Lower concentrations of each antibody (1 ug/ml) had the similar effect as 5 ug/ml, suggesting that the motility inhibitory effect can be further enhanced by a multivalent vaccine, diversifying the binding sites for antibodies on the CatSper channel.

Methods and system according to some embodiments of the present disclosure are directed to a contraceptive vaccine for providing long-lasting yet reversible contraceptive effects. The structure of the contraceptive vaccine stimulates an immune response to antigens present only in sperm cells, with the resulting anti-sperm antibodies effective to bind sperm and render those cells incapable of fertilization. The production and use of the contraceptive vaccine are simple. The need for hormone treatment and/or surgery are avoided as no action beyond vaccination is necessary to realize the benefits of the compositions of the present disclosure. Finally, the contraceptive immunity is easily and immediately reversible, with the immunity returning automatically to the contraceptive state with time as well.

Although the invention has been described and illustrated with respect to exemplary embodiments thereof, it should be understood by those skilled in the art that the foregoing and various other changes, omissions and additions may be made therein and thereto, without parting from the spirit and scope of the present invention.

---

---

What is claimed is:

1. A contraceptive chimeric virus-like particle, comprising:

an antigenic carrier domain; and one or more antigenic regions from a sperm cell in the antigenic carrier domain, wherein the antigenic carrier domain includes one or more capsid proteins, and the one or more capsid proteins include L1 from human papillomavirus, and wherein CGP amino acid residues are adjacent the N-terminal end of the one or more antigenic regions and GPC amino acid residues are adjacent the C-terminal end of the one or more antigenic regions.

2. The chimeric virus-like particle according to claim 1, wherein the one or more antigenic regions include structural elements of the Catsper ion channel complex.

3. The chimeric virus-like particle according to claim 2, wherein the structural elements include at least a portion of one or more loops positioned between the transmembrane helical segments of the Catsper ion channel complex.

4. The chimeric virus-like particle according to claim 3, wherein the structural elements include at least a portion of: the loop between Catsper1 s1 and Catsper1 s2, the loop between Catsper2 s5 and Catsper2 p-loop, the loop between Catsper1 s3 and Catsper1 s4, the loop between Catsper2 s1 and Catsper2 s2, the loop between Catsper3 s1 and Catsper3 s2, the loop between Catsper1 s5 and Catsper1 p-loop, the loop between Catsper2 p-loop and Catsper2 s6, the loop between Catsper3 s3 and Catsper3 s4, the loop between Catsper3 s5 and Catsper3 p-loop, the loop between Catsper3 p-loop and Catsper3 s6, the loop between Catsper4 s1 and Catsper4 s2, the loop between Catsper4 p-loop and Catsper4 s6, Catsper4 loop 785-805, Catsper5 loop 331-348, or combinations thereof.

5. The chimeric virus-like particle according to claim 4, wherein the virus-like particle includes SEQ. ID. NO.: 1, SEQ. ID. NO.: 2, SEQ. ID. NO.: 3, SEQ. ID. NO.: 4, SEQ. ID. NO.: 5, SEQ. ID. NO.: 6, SEQ. ID. NO.: 7, or combinations thereof.

6. A method for providing contraceptive treatment to a patient, comprising:

preparing a composition including a contraceptive chimeric virus-like particle including an antigenic carrier domain and one or more antigenic regions from a sperm cell in the antigenic carrier domain; and administering the composition to a patient to heighten an immune response of the patient to the one or more antigenic regions, wherein the antigenic carrier domain includes 11 from human papillomavirus, and wherein CGP amino acid residues are adjacent the N-terminal end of the one or more antigenic regions and GPC amino acid residues are adjacent the C-terminal end of the one or more antigenic regions.

7. The method according to claim 6, wherein the one or more antigenic regions include structural elements of the Catsper ion channel complex, wherein the structural elements include at least a portion of: the loop between Catsper1 s1 and Catsper1 s2, the loop between Catsper2 s5 and Catsper2 p-loop, the loop between Catsper1 s3 and Catsper1 s4, the loop between Catsper2 s1 and Catsper2 s2, the loop between Catsper3 s1 and Catsper3 s2, the loop between Catsper1 s5 and Catsper1 p-loop, the loop between Catsper2 p-loop and Catsper2 s6, the loop between Catsper3 s3 and Catsper3 s4, the loop between Catsper3 s5 and Catsper3 p-loop, the loop between Catsper3 p-loop and Catsper3 s6, the loop between Catsper4 s1 and Catsper4 s2, the loop between Catsper4 p-loop and Catsper4 s6, Catsper4 loop 785-805, Catsper5 loop 331-348, or combinations thereof.

8. The method according to claim 7, wherein the one or more antigenic regions includes SEQ. ID. NO.: 8, SEQ. ID. NO.: 9, SEQ. ID. NO.: 10, SEQ. ID. NO.: 11, SEQ. ID. NO.: 12, SEQ. ID. NO.: 13, SEQ. ID. NO.: 14, SEQ. ID. NO.: 15, SEQ. ID. NO.: 16, SEQ. ID. NO.: 17, SEQ. ID. NO.: 18, SEQ. ID. NO.: 19, SEQ. ID. NO.: 20, SEQ. ID. NO.: 21, SEQ. ID. NO.: 22, or combinations thereof.

9. The method according to claim 6, wherein the composition is administered subcutaneously, intravenously, intranasally, or combinations thereof.

10. The method according to claim 6, further comprising:

administering a supplemental composition to the patient to reverse the effects of the composition, the supplemental composition including a reversal agent having a protein sequence substantially identical to that of the one or more antigenic regions.

11. The method according to claim 10, wherein the reversal agent includes one or more peptides, the one or more peptides include SEQ. ID. NO.: 8, SEQ. ID. NO.: 9, SEQ. ID. NO.: 10, SEQ. ID. NO.: 11, SEQ. ID. NO.: 12, SEQ. ID. NO.: 13, SEQ. ID. NO.: 14, SEQ. ID. NO.: 15, SEQ. ID. NO.: 16, SEQ. ID. NO.: 17, SEQ. ID. NO.: 18, SEQ. ID. NO.: 19, SEQ. ID. NO.: 20, SEQ. ID. NO.: 21, SEQ. ID. NO.: 22, or combinations thereof.

* * * * *